United States Patent [19]

Reiche et al.

[11] 3,970,711

[45] July 20, 1976

[54] METHOD OF PRODUCING GLYCOLS

[75] Inventors: Charles Ronald Reiche; Jerry A. Heckman, both of Beaumont, Tex.

[73] Assignee: PPG Industries, Inc., Pittsburgh, Pa.

[22] Filed: July 19, 1971

[21] Appl. No.: 163,579

[52] U.S. Cl. ............................. 260/635 E; 203/41; 260/615 R; 260/615 B; 260/637 R
[51] Int. Cl.² ................... C07C 29/00; C07C 29/24
[58] Field of Search .................... 260/635 E, 637 R; 203/41

[56] References Cited
UNITED STATES PATENTS

| | | | |
|---|---|---|---|
| 2,135,271 | 11/1938 | Bolcar | 260/635 E |
| 2,327,779 | 8/1943 | Fisher et al. | 203/41 |
| 2,409,441 | 10/1946 | Metzger | 260/635 E |
| 2,756,241 | 7/1956 | Courter | 260/635 E |
| 2,839,588 | 6/1958 | Parker | 260/635 E |
| 3,311,544 | 3/1967 | Riehl et al. | 260/637 R |
| 3,367,847 | 2/1968 | Pierson | 203/41 |
| 3,408,267 | 10/1968 | Miller et al. | 203/41 |
| 3,458,583 | 7/1969 | Taul et al. | 260/637 R |
| 3,576,890 | 4/1971 | Binning | 260/635 E |

OTHER PUBLICATIONS
Kirk–Othmer, "Ency. of Chem. Techn.," vol. 8, 2nd ed., (1965), pp. 534–545.

*Primary Examiner*—Joseph E. Evans
*Attorney, Agent, or Firm*—Irwin M. Stein; John E. Curley

[57] ABSTRACT

A method of improving the quality of ethylene glycols, particularly monoethylene glycol which is derived from ethylene oxide produced by the direct oxidation of ethylene with air or oxygen is described. The novel method involves the removal of certain impurities from the ethylene oxide producing reaction system prior to the final processing of the ethylene oxide produced to glycol products. In a particular embodiment contaminating impurities are removed from a purge stream taken from the ethylene oxide reaction system and which is utilized in the ethylene glycols reaction system. Removal of the impurities by the preferred method of carbon adsorption produces in the ethylene glycols reaction system, glycols which have improved ultraviolet light transmittance. In particular, monoethylene glycol having an ultraviolet light transmittance rendering it suitable for use in fiber making processes is produced.

4 Claims, 1 Drawing Figure

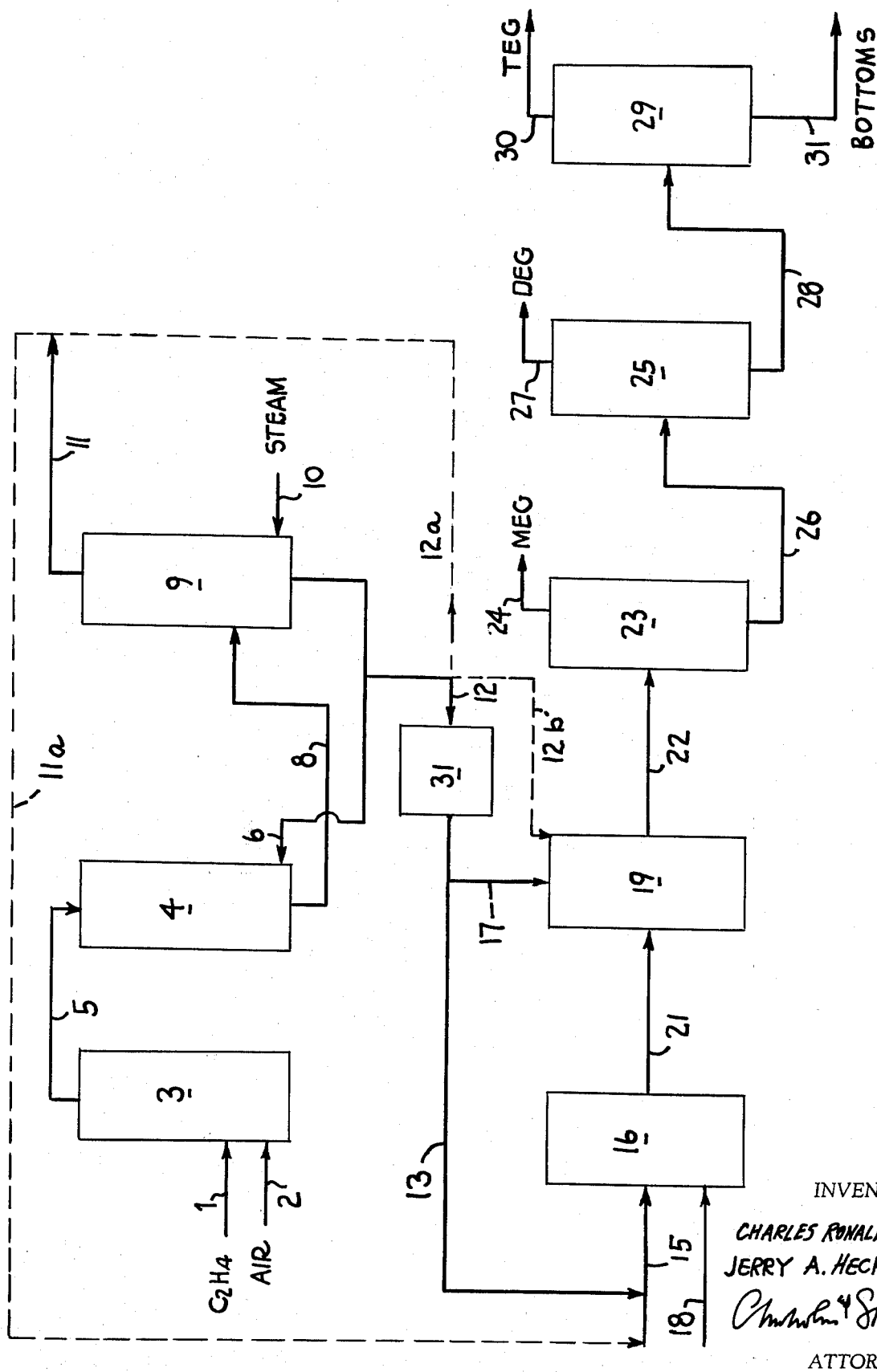

METHOD OF PRODUCING GLYCOLS

BACKGROUND OF THE INVENTION

Ethylene glycols (monoethylene glycol, diethylene glycol and triethylene glycol) are prepared commercially by several methods. One of these methods involves a two-stage reaction system, the first stage of which requires the direct oxidation of ethylene with air or elemental oxygen over a suitable catalyst, typically a silver-containing catalyst, at elevated temperature (100° to 500°C. is typical) and at superatmospheric pressure (2 to 25 atmospheres).

Ethylene oxide produced in these reactors, which may be fixed or fluid bed reactors as typified by U.S. Pat. Nos. 2,125,333 and 2,430,443, is removed from the reactors in a gas stream and is passed into an absorbing vessel where it is contacted with water to absorb the ethylene oxide content thereof. The gases (which still contain appreciable quantities of ethylene) are then recycled to the reactor while the ethylene oxide containing water in the absorbing vessel is passed to a stripping column. In the stripping column steam or hot water is introduced and contacted usually countercurrent to the ethylene oxide fed thereto to remove ethylene oxide product overhead. The water discharged from the stripping vessel is recirculated to the absorbing vessel for use in absorbing ethylene oxide therein.

In other systems a steam heated reboiler is employed to heat water in the bottom of the stripping column and boil it. This generates steam internally in the stripping column. While this eliminates a water build-up problem glycols still accumulate in the column and must be purged to the evaporation and/or recovery systems of the glycol producing unit.

As will be readily understood by the skilled artisan, the introduction of water into the stripping column and the closed recycle system between the stripping vessel and the absorbing vessel causes a buildup of water in the system requiring a purge to remove excess water. This purge stream contains appreciable quantities of ethylene glycol in it and is usually of such value that it cannot be discarded. Further, since it contains ethylene glycol, it cannot be easily disposed of due to the fact that ethylene gylcol has a deleterious effect of the total oxygen demand of bodies of water in which this material might be discharged. Similarly, where heated stripping vessels are used glycol buildup in the columns required a bleed of water-glycol from the system.

In a typical glycol plant in which ethylene oxide is hydrolyzed in a reaction zone with water at elevated temperature and pressure as the second stage of a reaction system and in which system glycols are subsequently evaporated and distilled to produce the pure glycols those waste streams are fed to the glycol reaction system to avoid the overall loss of glycols that accompanies disposal of glycol containing streams. These streams may be fed to any of several places in this second stage reaction system which is typically provided with a glycol reactor in which the oxide feed is converted to glycols, an evaporation system in which the glycols are concentrated and a still system in which all water is removed and in which monethylene glycol, diethylene glycol and triethylene glycol are separated from each other.

It has been found that the glycols produced when these water streams containing ethylene glycol are utilized in the glycols reaction system usually have an ultraviolet light absorption characteristic such that they are not suitable for use in the manufacture of polyester fibers. This limits the use of the product. Polyester fibers may be produced by reaction of ethylene glycol and terephthalic acid for example and limitation on the use of the glycols produced for this purpose presents a serious problem to the producer of glycols since a significant and desirable product market is thus lost.

THE PRESENT INVENTION

In accordance with the instant invention it has been discovered that waste water from an ethylene oxide, direct oxidation reaction system which contains ethylene glycol also contains contaminating impurities which, when utilized in the glycol producing stage of a glycol producing plant using ethylene oxide produced by direct oxidation of ethylene, causes the glycol product produced in the glycol stage to have low ultraviolet light transmittance values rendering it unsuitable for use as fiber grade glycol. Impurities discovered in these ethylene glycol-water streams which have been identified are mesityl oxide and ethylene carbonate. While not certain of the exact compound which is causing the low ultraviolet transmittance, it is theorized that mesityl oxide is the most likely compound. This theory is based on the fact that when this compound is removed from streams containing it, the ultraviolet light transmittance of the stream is improved. Further, when mesityl oxide is added in minute quantities (1 ppm or less) to pure monoethylene glycol having a good ultraviolet transmittance, the transmittance is immediately affected and is much lower than it was before addition.

In performing the instant invention the impurities in the ethylene glycol-water stream causing low ultraviolet light transmittance in monoethylene glycol product, for example, produced in a plant using this stream are removed from the stream prior to feeding them to the glycol reaction system. Effectiveness of the removal of impurities in the particular method employed is easily determined by measuring the ultraviolet light transmittance of monoethylene glycol manufactured in the plant using the contaminated water-ethylene glycol streams. Ultraviolet light transmittance is determined by comparison of the percent transmittance of ultraviolet light through the glycol sample at wave lengths of 220, 250, 275 and 350 nanometers compared to percent light transmittance at the same wave lengths through distilled water.

In accordance with the preferred mode of performing the instant method, an ethylene glycol-water stream recovered from an ethylene oxide reaction system using direct catalytic oxidation of ethylene with air or oxygen is treated before passage into a glycol reaction system producing ethylene glycols from the ethylene oxide made in the ethylene oxide reaction system by passing the ethylene glycol-water stream through a bed of activated carbon. Passage of the stream through a bed of activated carbon reduces the mesityl oxide content of the stream substantially or eliminates it. The bed also reduces or eliminates the ethylene carbonate content of such stream. The ethylene glycol-water mixture upon emerging from the carbon bed is found to have a high ultraviolet transmittance and the mixture may be fed to the glycol reaction system for recovery of its ethylene oxide content. It is also found that glycols produced in a glycol reaction system utilizing an ethylene glycol-water stream treated as described with activated carbon, produced monoethylene glycol having ultraviolet absorption characteristics rendering it suitable for use in fiber making. The carbon bed utilized is further found to remove the bothersome impurities causing low ultraviolet transmittance in the produced glycols for long periods of time before becoming exhausted. The carbon beds after exhaustion may be regenerated by use of high pressure steam or by recourse to heat treatment in a furnace if desired.

Ethylene glycol-water streams containing the contaminating impurities may be treated in accordance with this invention by recourse to several procedures other than the preferred method above described. Thus, these streams may be heat treated at elevated temperatures to eliminate the contaminating impurities by the thermal decomposition. Ethylene glycol-water streams containing the contaminating impurities can be heated under pressure (2 to 10 atmospheres or more) at temperatures of 250° to 400°C. to accomplish the decomposition. As reported in Whitmore, *Organic Chemistry*, at page 277, D. Van Nostrand Company, Inc., mesityl oxide may also be treated with HOCl to produce $Me_2C(OH)CHClCOM_e$. This product can be reacted with alkali to produce an insoluble epoxide that can then be filtered from the stream.

In the preferred mode of operation to remove the impurities deleteriously affecting glycol ultraviolet transmittance, monoethylene glycol in particular, a bed of adsorbent material is utilized. This method of removal has been found to require a minimum of equipment and material and accomplishes the result in an effective as well as economical manner. While the sewering of ethylene glycolwater mixtures containing contaminating impurities will prevent the introduction of those particular impurities into a glycol reaction system, the ethylene glycol-water streams representing a valuable process stream are thereby lost. This introduces a serious economic loss in the overall process. Still further, sewering of these materials represents a serious pollution problem in that they contain materials that seriously affect the biological oxygen demand and even possibly the chemical oxygen demand of the water bodies into which sewer waters are normally discharged.

The carbon beds utilized in the preferred mode of purification contemplated may contain any form of adsorbent carbon. Activated carbon has been found to be particularly effective for use in this purification and any activated carbon appears to be effective. The mesh size of the activated carbons of the preferred embodiment does not appear to be of particular significance and generally carbons ranging between 4 to 100 mesh are used. It is preferred that carbon in a size range of 4 to 40 mesh be utilized.

The process streams treated in accordance with this invention are typically in a temperature range of between 80° to 140°F., but preferably are maintained at a temperature of 85°F. or more, usually 85° to 95°F. It has been found that at temperatures below 80°F. the removal of the impurities from the ethylene glycol-water streams causing the ultraviolet transmittance difficulties is erratic in that the monoethylene glycol produced in the plant using these streams is acceptable some times and unacceptable other times with respect to ultraviolet transmittance. Thus, it is important that the temperature of the stream entering the carbon absorption system be above at least 80°F. and preferably above about 85°F.

While carbon, and activated carbon in particular, is described as the adsorbent used in practicing the instant invention, recourse to the use of other adsorbents may be had without departing from the spirit of the invention. Thus utilization of silica, silica gels, alumina, Fullers earth, porous glass such as leached borosilicate glass, diatomaceous earth and the like are contemplated.

For a more complete understanding of the invention, reference is made to the accompanying drawing which diagrammatically illustrates one method of producing glycols utilizing the instant invention.

In the drawing ethylene and air are fed to a reactor 3 through lines 1 and 2, respectively. The reactor 3 is a conventional fixed bed reactor containing a plurality of tubular reactors filed with a silver catalyst. The ethylene and oxygen react in the presence of the catalyst at temperature typically in the range of 100° to 500°C., preferably in the range of 200° to 360°C. The ethylene oxide produced is then passed to an absorber 4 via line 5 where it is contacted with water entering column 4 via line 6. Product ethylene oxide in water is removed via line 8 and is passed to a stripping vessel 9. In vessel 9 the ethylene oxide-water mixture is contacted with steam introduced in column 9 via line 10 and product ethylene oxide is removed via line 11 where it is passed to a fractionator, not shown, for further processing and fed to glycol reactor 16 via line 11a. This portion of a conventional ethylene oxide process is shown in Kirk Othmer, Vol. 5, pages 919–920, Interscience Publishers, Inc., New York, N. Y., 1950.

Water recovered in column 9 is recirculated in line 6 to column 4 where further quantities of ethylene oxide are absorbed in it. The steam addition in line 10, coupled with the recirculation of process waters, requires a bleed of water from the system in order to maintain a water balance. This stream is taken from line 6 in line 12 and since it contains typically from 0.2 to 3 or more percent ethylene gylcol in it, it is conventionally sent to a glycol producing plant via lines 12a and 11a to the ethylene oxide feed line 15 of reactor 16 for recovery. This stream may also be fed in a conventional manner via line 12b to the evaporator system 19.

The system 19 is typically a multiple effect evaporator system for steam economy purposes and in the preferred operation of this system with the ethylene oxide plant shown, the water stream in line 12b is fed to the third effect evaporator of the evaporator system 19 as reflux to that evaporator effect. Typically system 19 is a triple effect evaporator system.

Water is fed to the glycol reactor 16 via line 18 and the ethylene glycol products made in reactor 16 (monoethylene glycol, diethylene glycol and triethylene glycol) are removed via line 21 and fed to the evaporator system 19.

From the evaporator system 19 the product glycols are passed in line 22 to a monoethylene glycol still 23. In this still monoethylene glycol product is removed overhead in line 24. The bottoms of still 23 are sent to a second still 25 via line 26 and in this still diethylene glycol is removed overhead in line 27. The bottoms of this still are sent via line 28 to a third still 29 where they are processed and triethylene glycol product is removed via line 30. The bottoms of this still are removed via line 31 for further processing.

In the glycol distillation system illustrated, it is typical at atmospheric pressure to operate column 23 at bottoms temperatures of 230° to 250°C. and overhead temperatures of 190° to 200°C. Column 25 is operated at bottoms temperatures of about 260° to 283°C. with overhead temperatures of 220° to 250°C. and column 29 is usually operated with bottoms temperatures of 277° to 308°C. and overhead temperatures of 260° to 283°C.

In practicing the preferred embodiment of the instant invention with a glycol production unit using ethylene oxide produced by a direct oxidation system, the ethylene gylcol-water mixture in line 12 coming from the ethylene oxide plant is first treated in unit 31 to remove impurities therein to a level that does not contaminate the monoethylene glycol product to the extent that its ultraviolet absorption specifications are unacceptable for fiber grade use. This treatment in the preferred mode of operation constitutes an adsorption of the impurities in the product on an activated carbon bed. The ultraviolet light absorption characteristics of the water entering the bed 31 and leaving the bed 31 are measured. In addition the ultraviolet light characteristics of the monoethylene glycol recovered in line 24 of the still 23 are measured to insure good bed operation. The water removed from this bed may be fed to the glycol reaction system via line 13 to the glycol reactor 16 or via line 17 to the evaporation system 19, preferably the third effect of a triple effect evaporator as reflux therein.

In general it has been found that transmittance of ultraviolet light in the water stream in lines 13 or 17 of at least 94 or more at wave length of 250 nanometers will provide for a monoethylene glycol product from still 23 having a transmittance within an acceptable range for fiber grade use, i.e., 75 to 76 at 220 nanometers, 88 to 90 at 250 nanometers, 90 to 92 at 275 nanometers and 98 to 99 at 350 nanometers.

For a more complete understanding of the instant invention, reference is made to the following example which illustrates the instant invention utilized to produce monoethylene glycol of fiber grade quality from a glycol installation using ethylene oxide produced by air oxidation of ethylene and recovering ethylene glycol-water streams from the ethylene oxide plant as part of the feed to the glycol plant.

EXAMPLE

A purge stream 12 containing ethylene glycol-water mixture from an ethylene oxide plant such as illustrated in the accompanying drawing and which averaged 30 to 35 gallons per minute in volume flow was passed into the top of a carbon bed contained in a 6 foot diameter pressure vessel. The bed was packed with a Pittsburgh Activated Carbon, Type Cal, 12 to 40 mesh in size, manufactured by Calgon Corporation to a depth of 4 feet. The vessel 31 was 8 feet in height and the bed was placed on a screen about 1 foot from the bottom of the vessel 31. The process glycol-water mixture. in line 12 was passed through the bed and the vessel 31 was filled and maintained at an internal pressure of 125 psig. The process water after passage through the carbon bed was utilized as reflux in the evaporator system 19 in the third effect evaporator of a glycol plant as illustrated and which used the ethylene oxide produced in the reaction system shown as feed to the glycol reaction system shown. Glycol was produced in vessel 16 by reacting ethylene oxide and water at a temperature of about 100° to about 120°C. and at a pressure of about 8.3 atmospheres. The glycol was evaporated in unit 19 and monoethylene glycol was distilled in column 23 at atmospheric pressure with a bottoms temperature of about 246°C. and an overhead temperature of about 198°C. The monoethylene glycol product from the still 23 was monitored for its ultraviolet transmittance using distilled water as the reference liquid in a Beckman Model DU 2400 Spectrophotometer. The results of the treatment on the purity of the monoethylene glycol produced while the carbon bed was employed are shown below in Table I:

TABLE I

| Run* | Wavelength (nanometers) | | | |
|---|---|---|---|---|
| | 220 | 250 | 275 | 350 |
| 1 | 80 | 89 | 92 | 100 |
| 2 | 80 | 91 | 94 | 100 |
| 3 | 82 | 92 | 94.5 | 100 |
| 4 | 81 | 90 | 94 | 100 |
| 5 | 81 | 91 | 93 | 100 |
| 6 | 79 | 90 | 92 | 100 |
| **Standard | 75 | 88 | 90 | 98 |

*Each run was sampled over a 16 hour period. Runs 1, 2, 4, 5 and 6 were sampled every 2 hours and Run 3 was sampled every 3 hours. The bed was used continuously with the runs not being monitored between midnight and 8 A. M.
**Monoethylene glycol having transmittance values shown is acceptable for fiber grade use. Higher numbers than those shown are improvements over the standard.

The carbon bed above described was used to treat ethylene glycol-water mixtures recovered from a direct oxidation of ethylene oxide until the bed no longer produced acceptable ultraviolet light transmittance in monoethylene glycol produced in a plant using such mixtures. The bed was found capable of processing 1.8 million gallons of such process ethylene glycol-water mixtures before it became exhausted.

While the invention has been described with reference to certain specific embodiments, it is not intended to be limited thereby except insofar as appears in the accompanying claims.

We claim:

1. In the process of producing ethylene glycol in an ethylene glycol reaction system by hydrolysis of ethylene oxide wherein ethylene oxide, which is produced by direct oxidation of ethylene, is absorbed in water in an absorbing vessel to form an ethylene oxide-water mixture, ethylene oxide is stripped from the ethylene oxide-water mixture in a stripping vessel, and ethylene glycol-containing water from the stripping vessel is recycled to the absorbing vessel, the improvement which comprises removing a portion of the ethylene glycol-containing water as a purge stream, improving the ultraviolet light transmittance of ethylene glycol-containing water purge stream by contacting it at a temperature of at least 80°F. with an adsorbent selected from the group consisting of carbon, silica, silica gel, alumina, Fuller's earth, porous glass and diatomaceous earth, forwarding ethylene glycol-containing water of improved ultraviolet light transmittance to the ethylene glycol reaction system and recovering ethylene glycol that is suitable for fiber manufacture from the ethylene glycol reaction system.

2. The process of claim 1 wherein the ethylene glycol-containing water purge stream contains from about 0.2 to about 3 percent ethylene glycol and the purge stream is contacted with adsorbent at from about 80° to about 140° F.

3. The process of claim 1 wherein the ethylene glycol reaction system contains a glycol reactor wherein ethylene oxide is hydrolyzed with water to ethylene glycols and an evaporator system wherein water is separated from the ethylene glycols, and wherein the ethylene glycol-containing water purge stream of improved ultraviolet light transmittance is forwarded to the glycol reactor, or to the evaporator system as reflux, or to both of said glycol reactor and evaporator system.

4. The process of claim 3 wherein the adsorbent is activated carbon.

* * * * *